(12) United States Patent
Hooper et al.

(10) Patent No.: US 8,056,205 B2
(45) Date of Patent: Nov. 15, 2011

(54) METHOD OF MANUFACTURING A REACTION VESSEL

(75) Inventors: Charles William Hooper, Cleveland (GB); Michael Peter Roberts, Cleveland (GB)

(73) Assignee: Johnson Matthey PLC, London (GB)

( * ) Notice: Subject to any disclaimer, the term of this patent is extended or adjusted under 35 U.S.C. 154(b) by 832 days.

(21) Appl. No.: 11/663,895

(22) PCT Filed: Sep. 2, 2005

(86) PCT No.: PCT/GB2005/003397
§ 371 (c)(1),
(2), (4) Date: Mar. 26, 2007

(87) PCT Pub. No.: WO2006/032839
PCT Pub. Date: Mar. 30, 2006

(65) Prior Publication Data
US 2008/0107584 A1  May 8, 2008

(30) Foreign Application Priority Data
Sep. 24, 2004  (GB) .................................. 0421198.3

(51) Int. Cl.
*B21D 39/03*  (2006.01)
(52) U.S. Cl. ............................ 29/428; 422/218; 585/820
(58) Field of Classification Search .................... 29/428; 422/218; 423/359, 415.1; 585/820
See application file for complete search history.

(56) References Cited

U.S. PATENT DOCUMENTS

| 2,861,873 | A | * | 11/1958 | Worn ............................ 422/148 |
| 4,033,727 | A | | 7/1977 | Vautrain |
| 4,126,539 | A | | 11/1978 | Derr, Jr. et al. |
| 4,298,589 | A | | 11/1981 | LeBlanc et al. |
| 5,670,116 | A | | 9/1997 | Gupta et al. |
| 2002/0102192 | A1 | | 8/2002 | Ward |

FOREIGN PATENT DOCUMENTS

| EP | 0 075 056 A1 | 3/1983 |
| EP | 0 217 513 A1 | 4/1987 |
| GB | 1 307 845 | 2/1973 |
| WO | WO-2004/033084 A1 | 4/2004 |

* cited by examiner

*Primary Examiner* — Richard Chang
(74) *Attorney, Agent, or Firm* — RatnerPrestia (57) ABSTRACT

A method of adapting an axial flow reaction vessel having opposed ports to an opposed axial flow reaction vessel includes installing a process fluid collection system centrally within the body of the vessel in fluid communication with one or more outlet ports of the ports; wherein said process fluid collection system includes a perforate member defining a chamber and a conduit in fluid communication with the chamber, the conduit being adapted for attachment to the one or more outlet ports, providing the vessel with a bed of particulate catalyst or sorbent around said process fluid collection system; and adapting a feed to the vessel through one or more inlet ports of the ports such that a process fluid fed to the vessel is passed axially and in an opposite direction through the fixed bed of catalyst or sorbent and is collected by the process fluid collection system.

7 Claims, 5 Drawing Sheets

METHOD OF MANUFACTURING A REACTION VESSEL

This application is the U.S. National Phase application of PCT International Application No. PCT/GB2005/003397, filed Sep. 2, 2005, and claims priority of British Patent Application No. 0421198.3, filed Sep. 24, 2004.

FIELD OF THE INVENTION

This invention relates to a method and apparatus for adapting an axial flow reaction vessel to opposed axial flow.

BACKGROUND OF THE INVENTION

Pressure drop is a phenomenon experienced when fluids are passed through particulate beds of catalyst or sorbent. In extreme cases pressure drop can lead to unacceptable increases in compression and pumping costs. Thus there is a desire to reduce pressure drop when process fluids are passed through reaction vessels containing fixed beds of catalyst or sorbent.

Reaction vessel configurations in which the pressure drop is reduced compared to simple axial flow reactors are known. Radial-flow reactors, for example as described in U.S. Pat. No. 4,033,727, typically comprise a cylindrical central conduit surrounded by an annular cylindrical catalyst bed bounded by perforate catalyst restraining means defining an annular cylindrical void between the catalyst bed and the interior of the vessel wall. The complexity of such radial flow reactor designs can make them expensive and difficult to install.

Opposed-axial flow reaction vessels offer an operator of a process wherein a process fluid is passed axially through a bed of catalyst or sorbent disposed within a vessel, the ability to reduce the pressure drop through the catalyst to approximately one-eighth of that obtained where the process fluid is conducted through the whole length of the catalyst bed.

EP 075056 describes a split axial flow converter for the low-pressure synthesis of ammonia. The converter comprises a reaction vessel containing an ammonia synthesis catalyst with opposed first and second inlet ports and gas collection means disposed approximately centrally within the catalyst bed. The gas collection means comprise a number of perforate concentric rings bisected by an outlet pipe that exits the reactor radially at the level of the concentric rings. Such a design, while effective in reducing pressure drop uses gas collection means that are unsuitable for fitting to an existing reactor and are of limited versatility. In particular the outlet pipe extending radially through the reactor wall reduces the pressure-bearing ability of the reaction vessel and its installation into an existing vessel presents considerable difficulties in stress-relieving the vessel prior to use.

GB 1307845 describes an ammonia or methanol synthesis reactor comprising a catalyst bed space defined by two coaxial hollow cylinders, the inner cylinder comprising two portions one of which is greater in diameter than the other and a heat exchanger occupying at least part of the portion of greater diameter. In a preferred form of the reactor the outlet of the cold side of the heat exchanger is in flow communication with separated inlets at the top and bottom of the catalyst bed so that the stream of incoming gas leaving the heat exchanger is divided, one part being led to the top of the catalyst bed, the other part being led to the bottom of the catalyst bed, whereafter the two flows meet and leave by a bed outlet disposed in the catalyst bed at an intermediate position which may be near to the inlet to the 'hot' side of the heat exchanger. Such a design is complex, difficult to fabricate and is unsuitable for fitting to an existing reactor.

Thus there is a need for a method to adapt an axial flow reaction vessel to an opposed flow reaction vessel that comprises providing process fluid collection means that are simple to fabricate and which utilizes existing inlet and outlet ports.

SUMMARY OF THE INVENTION

Accordingly the invention provides a method of adapting an axial flow reaction vessel having opposed ports to an opposed axial flow reaction vessel comprising installing process fluid collection means within the body of the vessel in fluid communication with one or more of said ports.

The invention further provides process fluid collection means suitable for use in the above method comprising a perforate member defining a chamber and a conduit in fluid communication with said chamber, said conduit being adapted for attachment to one or more existing opposed ports of an axial flow reactor.

The invention further provides an opposed axial flow reaction vessel comprising the above process fluid collection means and a process comprising the steps of
(i) feeding a process fluid to one or more opposed ports of the reaction vessel,
(ii) passing the process fluid axially and in the opposite direction through a fixed bed of catalyst or sorbent disposed within the vessel,
(iii) collecting the resulting process fluid via collection means situated within said fixed bed, and
(iv) removing the process fluid from the vessel via said collection means, said collection means being in fluid communication with one or more existing opposed ports in said vessel.

The axial flow reaction vessel suitable for adaptation according to the method of the present invention comprises a shell, which may be circular or another shape in cross-section, and which may or may not be jacketed, having opposed ports. By 'opposed ports' we mean that the ports to the reaction vessel are disposed at either end of the vessel. Such reaction vessels, particularly those operated at pressure have domed ends in which the ports are located. These ports may comprise the original opposed process fluid inlet and outlet ports, but may also include other ports such as inspection ports, access ports, thermocouple ports and catalyst charging or discharging ports.

BRIEF DESCRIPTION OF THE DRAWINGS

The invention will now be described with reference to the accompanying drawings in which.

DETAILED DESCRIPTION OF THE INVENTION

In the present invention, process fluid collection means are installed within the reaction vessel and connected to one or more of the existing opposed ports. In operation of one embodiment according to the invention, the process fluid is divided and portions fed to opposite ends of the vessel. In another embodiment, the entire process fluid is fed to one end of the vessel and bypass means located within the vessel convey a portion of the process fluid to the other end. The process fluid then passes through the bed of catalyst or sorbent disposed in the vessel in opposite directions and is collected by the process fluid collection means which then convey it from the vessel via one or more of the existing opposed ports. The fixed beds are subject to axial flow and may be disposed, for example, substantially horizontally in the vessel with process fluid passing substantially vertically through the bed.

The optimum reduction in pressure drop is obtained where 50% of the process fluid passes through an equal thickness of particulate catalyst or sorbent before reaching the process fluid collection means. Thus whereas the process fluid collection means may be installed at any position between the opposed ports, in order to maximize the benefit of the opposed-axial flow configuration, the process fluid collection means are preferably installed approximately equidistant between said opposed ports, i.e. the collection means are preferably disposed centrally within the bed with in the reaction vessel.

The process fluid collection means may comprise any collection means suitably adapted for collection of the process fluid. The collection means should be designed to ensure even collection of process fluid from the catalyst bed to avoid by-passing part of the catalyst or sorbent. Preferably the process fluid collection means comprise a perforate member defining a chamber and a conduit in fluid communication with said chamber, said conduit being adapted for attachment to one or more of said ports. Suitable perforate members are perforate tubes, plates or meshes that may maximize their surface area by having corrugated surfaces. The chambers defined by the perforate members may be in fluid communication with one or more non-perforate conduits that convey process fluid to one or more outlet ports.

The perforate member is preferably tubular as this permits ready fabrication and assembly. The tubular perforate member may take the form of one or more perforate tubular arms radiating from the conduit. Preferably the arm or arms are in fluid communication with one or more perforate tubular rings lying in the plane of the arm or arms. Such a perforate ring collector may comprise one, two or more rings that may be circular, oval, or polygonal such as triangular, square, pentagonal, hexagonal, heptagonal or octagonal. The ring or rings may be continuous or discontinuous. Polygonal configurations may permit more ready fabrication and construction than circular or oval shapes. The size of the perforate collection means will depend upon the duty it is to perform and the ease with which it may be installed, however perforate ring collectors may preferably have an outer diameter between 50 and 90% of the diameter of the reaction vessel. The perforations in the perforate member may be holes or lateral cuts made by conventional means. Whichever is chosen, the perforations should be designed such that the particulate catalyst or sorbent does not pass through, for example by appropriate sizing of the perforations or by covering the perforations with a suitable material such as a wire mesh.

A feature of the present invention is that the process fluid collection means should readily be fabricated and installed in the reaction vessel. Access to the reaction vessel may be by removal of one of the domed ends or preferably via an access port or 'manhole'. The present invention is particularly suitable for adaptation of large high-pressure reaction vessels with out removal of the domed ends. This requires that the process fluid collection means are able to fit through such ports and in a preferred embodiment the process fluid collection means are in modular form. Thus the collection means may comprise a number of suitably sized parts that may be joined together in-situ within the vessel by means of flanged joints, welds or clamps. Welding is less preferred in reaction vessels that are to be operated at elevated pressures because of the subsequent need for stress relieving prior to operation. The preferred embodiments of the present invention avoid the need for welding to the thick-walled pressure shell and restrict any welding to either thin-walled parts external to the vessel where external stress relief may be applied more easily or in some cases avoided completely.

In one embodiment where the axial-flow reaction vessel has multiple opposed ports suitable for adaptation, the process fluid collection means are installed in fluid communication with two or more outlet ports. This has the advantage that the pressure drop using two or more outlet ports can be lower than using one port.

In an alternative embodiment where the axial-flow reaction vessel has only two opposed ports suitable for adaptation, (i.e. one at each end) the process fluid collection means may be installed in fluid communication with an outlet port, said outlet port being in concentric arrangement with an inlet port. By 'concentric arrangement' we mean that the outlet port is formed within the inlet port, which is therefore annular. We have found that this arrangement may be improved by providing the outlet port with venturi means where it is concentric to the inlet port. The venturi means comprises a constriction in the outlet port followed by a gradual enlargement. The gradual enlargement allows recovery of the pressure energy downstream of the constriction. We have found that including venturi means in this embodiment permits the outlet port to be narrower in diameter without incurring increased pressure drop caused by the higher velocity of gas. At the same time, the annular inlet port is less restricted than the case where the outlet port is conventional straight piping.

In another embodiment where the axial-flow reaction vessel has only two opposed ports suitable for adaptation, (i.e. one at each end), the fluid collection means may be in fluid communication with the outlet port and catalyst or sorbent bypass means may be provided in the reaction vessel to convey a portion of the process fluid from the inlet end of the vessel to the outlet end, thus by-passing the bed of catalyst or sorbent disposed in between. In order for the process fluid to leave the vessel it must again flow in opposite directions through the bed of catalyst or sorbent to the process fluid collection means which are preferably disposed centrally within the bed. The bypass means may comprise, for example, cylinders forming an annulus within the bed or at its periphery with the vessel wall through which the process fluid may pass. Alternatively and preferably the by-pass means may be one or more, e.g. 1-20, by-pass tubes. The by-pass means may be sized to convey up to about 60% vol, preferably about 50% vol, of the process fluid from the inlet end of the vessel to the outlet end. It will be understood that where the process fluid collection means are not disposed centrally within the reactor, that the by-pass means may be suitable sized so as to supply a suitably balanced amount of process fluid to either end the bed to enable optimum efficiency to be obtained.

The by-pass means extend from above the bed of catalyst or sorbent to below it (or vice versa) and may be fabricated from any suitable material within the temperature and chemical constraints of the process.

The method of the present invention is particularly suited to adapt axial flow reactors containing beds of catalyst as it minimises the alterations to the shell of the vessel by utilizing the existing ports and catalyst restraining means already employed in an axial flow reactor. Hence the opposed-flow reaction vessels of the present invention are simpler to construct and, because they do not weaken the shell of the axial flow reactor, are more versatile than the radial or opposed flow vessels of the prior art.

In operation, the opposed-axial flow reaction vessel contains a fixed bed of particulate catalyst or sorbent. By the term "sorbent" we include both adsorbent and absorbent materials. The particulate catalyst or sorbent is typically in the form of spheres, platelets, cubes, extrudates, cylindrical pellets, rings, granules or other regular or irregular shapes, with average size below 25 mm preferably having an aspect ratio, i.e. the largest dimension divided by the smallest dimension, of less than 2. Preferably the pellets comprise multiple (e.g. 4) holes and flutes or lobes that further act to reduce the pressure drop through the fixed bed.

The catalyst or sorbent may be continuous through the bed or the bed may also comprise layers of inert material. For example, inert particles, e.g. in the form of spheres may, be used at one or both ends of the catalyst or sorbent bed, e.g. to support the weight of catalyst or sorbent. Preferably a layer of inert particles is provided around the process fluid collection means, more preferably the inert particles have a particle size greater than that of the catalyst or sorbent particles making up the remainder of the bed so that the permeability of process fluid in the region of the collection means is increased. This increased permeability improves the ability of the collection means to collect the process fluid once it has passed through the bed of catalyst or sorbent.

The reaction vessels adapted by the method of the present invention containing the process fluid collection means may be used for any processes where a reduction in pressure drop in an axial flow reactor containing a fixed bed of catalyst or sorbent is desired. The vessels are typically 1-10 meters in height and have diameters of 0.5-5 meters. The method of the present invention is particularly suitable for large pressure vessels $\geq 5$ meters in height and $\geq 2.5$ meters diameter. The operation of the adapted reactor comprises feeding a process fluid to the opposed axial flow reaction vessel, passing the process fluid axially and in the opposite direction through the fixed bed of catalyst or sorbent disposed within the vessel, collecting the resulting process fluid via collection means situated within said fixed bed, and removing the process fluid from the vessel via said collection means.

It will be understood that the duty of the opposed ports in the adapted reaction vessel may be the same or different from that before the vessel was adapted.

The process fluid may be liquid or gaseous but is preferably gaseous. To achieve a reduction in pressure drop, whilst maintaining the output from the reaction vessel, the process fluid fed to the opposed axial flow reaction vessel may be divided and fed to the opposed inlet ports. In an opposed axial flow reaction vessel in which the collection means are disposed mid-way between the inlet ports, the process fluid is preferably split 50:50, i.e. with half of the original flow being fed to each end of the vessel, but some variation of this is possible to take into account different packing of particulate catalyst or sorbent each side of the collection means or the position of the collection means within the catalyst bed. Alternatively, the entire process fluid may be fed to one inlet port and by-pass means, e.g. tubes, used within the vessel to convey, preferably about 50% of the process fluid to either end of the bed of catalyst or sorbent. The process fluid collection means may then be in fluid communication with one or more outlet ports opposed to the inlet port.

The opposed axial flow reaction vessels of the present invention are useful for reducing the pressure drop in ammonia production processes upstream of the ammonia synthesis stage. This has the advantage that the throughput of the whole process may be increased because we have found that increasing the throughput of an ammonia plant may be limited by pressure drop in the front end of the plant. Particularly suitable reaction vessels that may benefit from the opposed flow configuration of the present invention are the water gas shift vessels, e.g. high-temperature shift and low-temperature shift vessels, and methanator vessel. Accordingly in preferred embodiments, the vessels comprise beds of high-temperature shift, low-temperature shift or methanation catalysts.

The water gas shift reaction is well known and is used in synthesis gas generation processes often as part of hydrogen or ammonia synthesis processes to increase the hydrogen content of the gas stream. In the water gas shift reaction, the process fluid is a crude synthesis gas comprising carbon oxides, hydrogen and steam, which is passed at elevated pressure and a temperature in the range of about 350-500° C. over a high temperature shift catalyst such as a reduced chromia-doped iron catalyst and then if desired at lower temperatures below 300° C. over a reduced copper catalyst, e.g. a copper-zinc-alumina catalyst in a so called low temperature shift stage.

Methanation is typically used in ammonia processes to convert small amounts of carbon oxides residual in a hydrogen/nitrogen process fluid mixture to methane prior to feeding the mixture to the ammonia synthesis catalyst. This is done to protect the longevity of the iron-based ammonia synthesis catalyst, which is poisoned by carbon oxides. The methanation catalyst is typically a reduced nickel catalyst supported on a refractory support such as alumina or calcium aluminate doped with magnesia.

In particular, the process of the present invention is especially suitable for the production of methanol or ammonia, particularly methanol.

Methanol synthesis may be performed at pressures in the range 40-150, and more conveniently in the range 45-120, bar abs. The temperature is suitably in the range 160-300° C., with a catalyst bed outlet temperature preferably in the range 220-290° C. Such temperatures provide for an acceptable methanol output rate (owing to favourable equilibrium) without producing the greater content of by-product impurities that would result from operation at higher temperatures. The process fluid passed over the catalyst is often a mixture of fresh de-watered synthesis gas comprising carbon oxides and hydrogen and unreacted gas recycled from methanol recovery, but the process is also suitable for once-through operation, using a methanol-free de-watered synthesis gas mixture. The methanol synthesis catalyst is typically a reduced copper catalyst such as a copper-zinc-alumina catalyst, e.g. as described in EP0217513.

In ammonia synthesis, a hydrogen/nitrogen mixture is typically passed as process fluid over the ammonia synthesis catalyst at high pressure, e.g. in the range 80-300 bar abs and a temperature in the range 300-540° C. The ammonia synthesis catalyst may be an iron-containing catalyst such as a promoted iron catalyst.

The process of the present invention may also be applied to reaction vessels used for purification of gaseous feedstocks. For example, the process fluid may comprise a hydrocarbon feedstock containing catalyst poisons and the fixed bed then comprises a catalyst or sorbent useful for removing said poisons from the feedstock. Typical catalyst poisons include compounds of sulphur, mercury, arsenic or halide, e.g. chloride. In the case of sulphur compounds the fixed bed may comprise a hydrodesulphurisation catalyst and/or a bed of hydrogen-sulphide absorbent. For removing mercury, arsenic or halide a sorbent material suitable for the removal of mercury, arsenic, or halide from hydrocarbons may be used. Hydrodesulphurisation of hydrocarbon feedstocks is typically carried out over cobalt-molybdenum catalysts and is usually followed by a step of hydrogen sulphide removal using a hydrogen sulphide sorbent. Examples of sorbents include basic zinc carbonate and copper and/or zinc oxides for sulphur removal, metal sulphides for mercury and arsenic removal and sodium aluminate or lead oxide or carbonate for halide (hydrogen chloride) removal.

Figure 3:
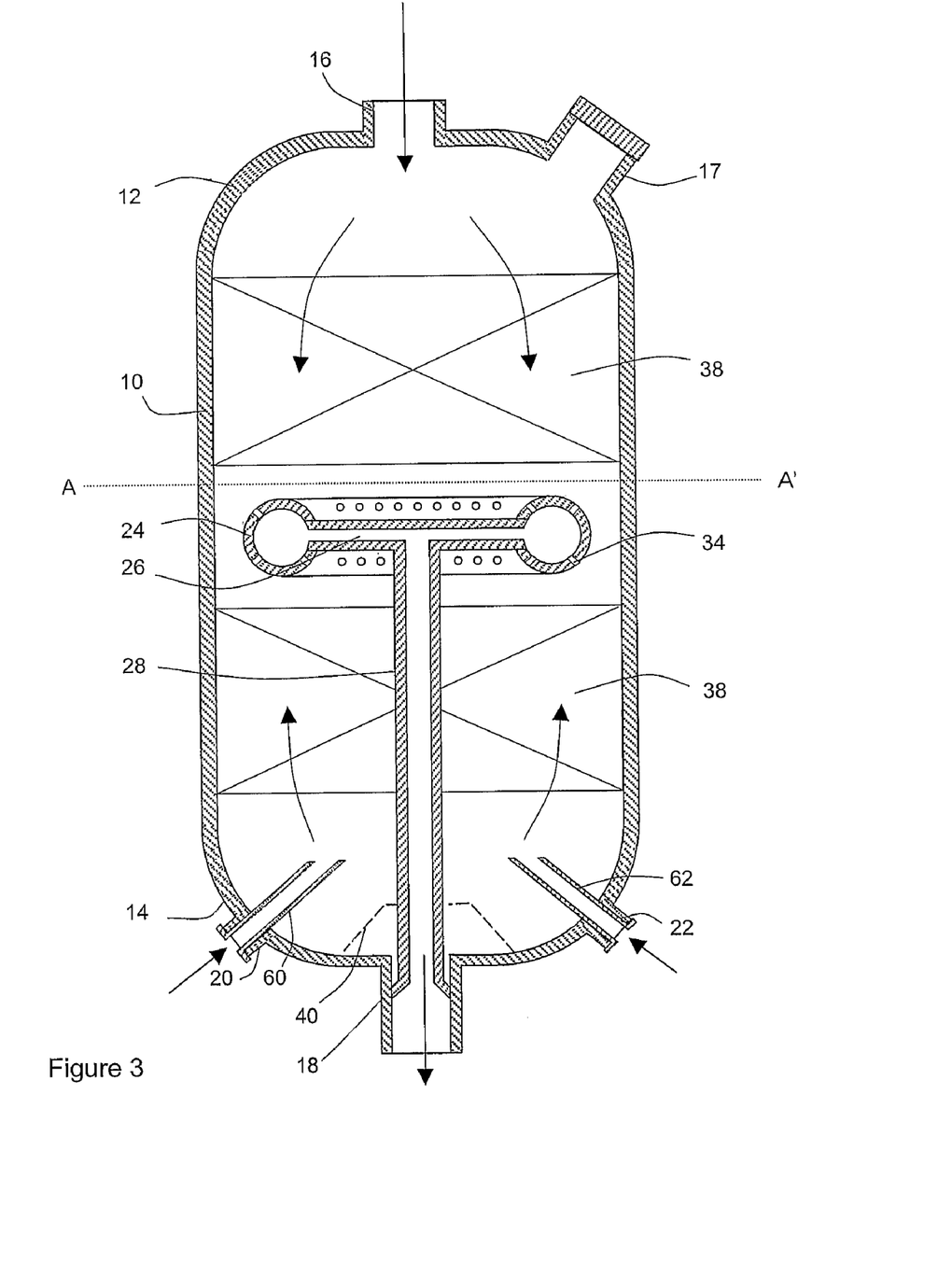
FIG. 3 is a diagrammatic vertical cross section of an opposed axial flow reaction vessel adapted according to a third embodiment of the present invention.
Figure 4:
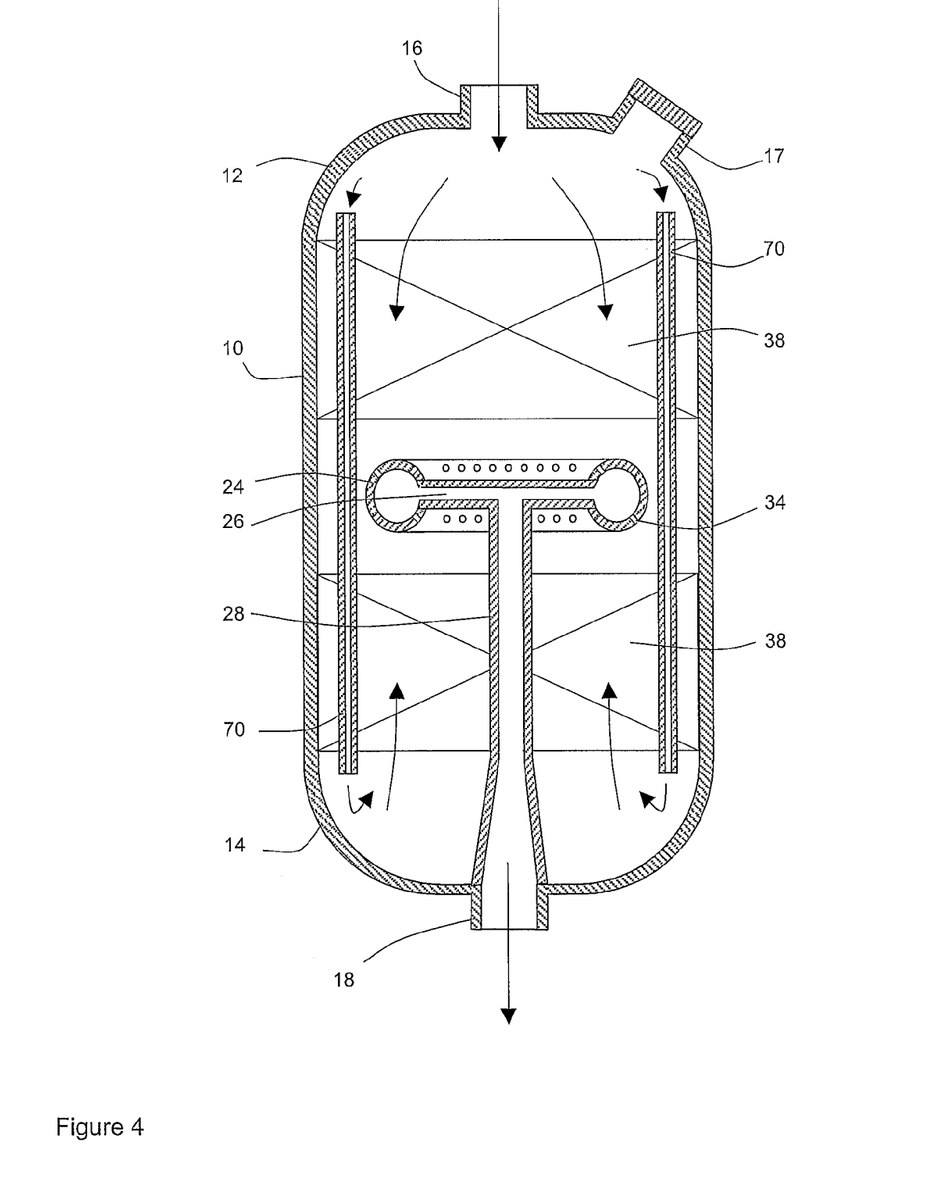
FIG. 4 is a diagrammatic vertical cross section of an opposed axial flow reaction vessel adapted according to a fourth embodiment of the present invention.
Figure 5:
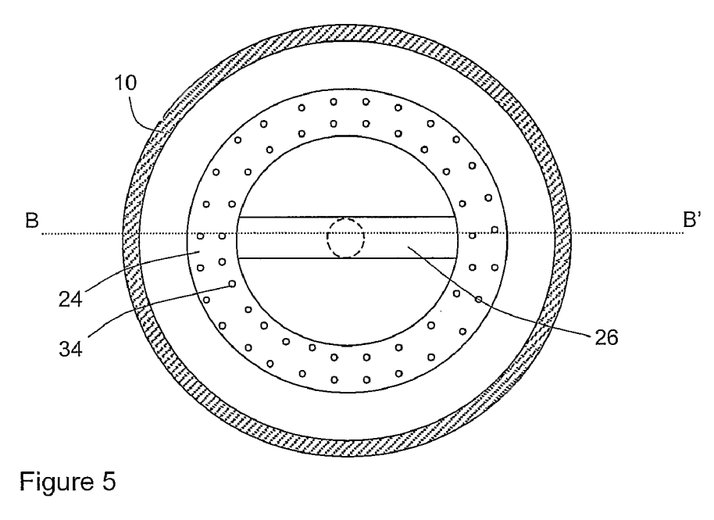
FIG. 5 is a horizontal cross section of the reaction vessels depicted in FIGS. 1, 2 and 3

In FIGS. 1, 2, 3 and 4, the vertical cross section is down line B-B' depicted in FIG. 5. This line bisects the reaction vessel approximately at its diameter and passes through the respective process fluid collection means. In FIG. 5, the horizontal cross section is along lines A-A' depicted in FIGS. 1, 2 and 3. In each case, these lines bisect the reaction vessels just above the process fluid collection means. For clarity, the flow of process fluid into and through the vessels in FIGS. 1, 2, 3 and 4 is depicted by way of arrows.

Figure 1:
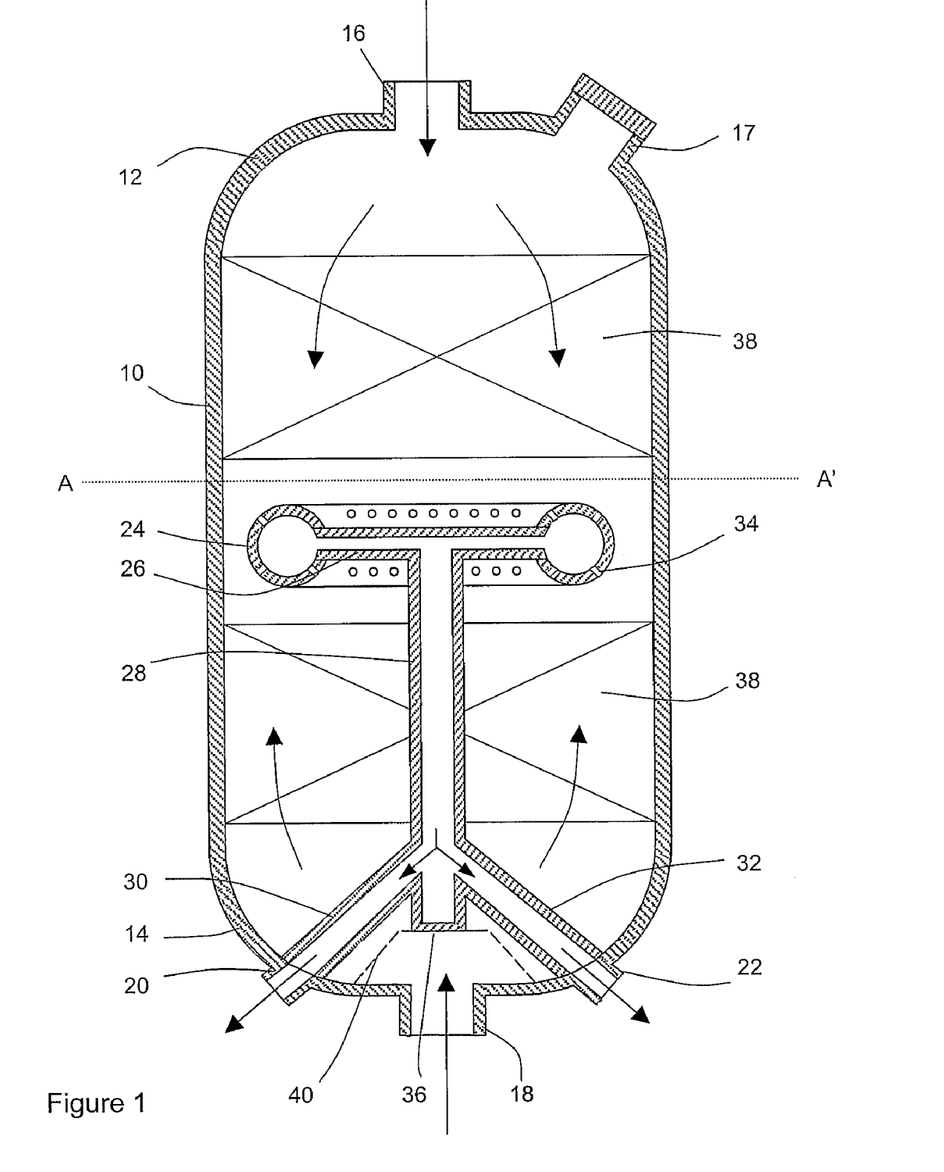
FIG. 1 is a diagrammatic vertical cross section of an opposed axial flow reaction vessel adapted according to a first embodiment of the present invention.

In FIG. 1, a reaction vessel suitable for methanol synthesis comprises a cylindrical shell 10, having domed ends 12 (top) and 14 (bottom). The domed end 12 has a process fluid port 16 and an access port 17, which in use is closed and sealed. The domed end 14 has three process fluid ports 18, 20 and 22 opposed to port 16. Port 18 is aligned on the same axis as port 16 whereas ports 20 and 22 are offset, one to either side of port 18. Prior to adaptation, ports 16 and 18 were process fluid inlet and outlet ports respectively and ports 20 and 22 were catalyst discharge ports.

Figure 6:
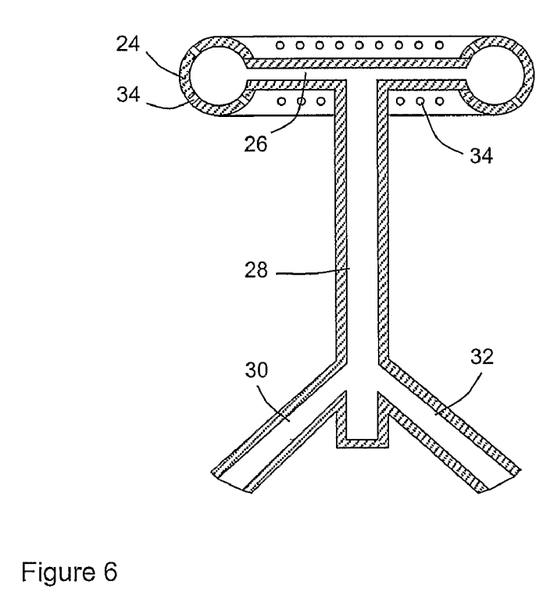
FIG. 6 is a diagrammatic cross section of process fluid collection means in accordance with the first embodiment.

As shown in FIG. 6, process fluid collection means suitable for installation in the reaction vessel comprise a perforate tubular ring collector 24 and conduits 26, 28, 30 and 32 in fluid communication with each other.

As depicted in FIG. 5, the perforate ring collector 24, comprises a continuous tubular ring coaxial with shell 10 and having a diameter about 70% of shell 10. The ring has a plurality of orifices 34 over its surface that permits ingress of process fluid into the ring. The dimensions of the ring and number, position and size of the orifices are such that even flow from the fixed bed into the collection means occurs. The ring is linked across its diameter by a non-perforate conduit 26 which is in fluid communication at either end with the inside of the tubular collector 24 so that process fluid may flow from the chamber inside of the collector into the conduit.

The tubular ring collector 24 lies on a plane perpendicular to the axis through the reaction vessel and is approximately equidistant between ports 16 and 18. The collector 24 and conduit 26 are supported by vertical conduit 28 aligned with the axis through the reactor and in fluid communication with conduit 26. The bottom of conduit 28 is closed and the closed end is supported on conduit supporting means 36 extending above port 18. The conduit supporting means advantageously comprises the perforate catalyst restraining means 40 present in the vessel prior to installation of the process fluid collector.

The conduit 28 is in fluid communication with conduits 30 and 32 that extend from the lower half of conduit 28 to connect to fluid ports 20 and 22 respectively.

Prior to use, a fixed bed of catalyst 38, e.g. 3×3 mm pellets of a copper-zinc-alumina methanol synthesis catalyst, may be charged through access port 17. Layers of inert alumina spheres (not shown) may be provided in domed end 14 to support the catalyst and around the tubular ring collector 24 by sequential addition. Preferably the alumina spheres have a larger diameter than the catalyst pellets to improve gas permeation through the bed.

In use, approximately equal amounts of dewatered synthesis gas comprising hydrogen and carbon oxides, optionally with unreacted gas recycled from methanol recovery, are fed into the vessel through opposed ports 16 and 18. Distributor means (not shown) distribute the gas entering via port 16 over the surface of the top of the catalyst bed. The perforate catalyst restraining means 40 which acts to prevent egress of the catalyst pellets from the reactor via port 18 also advantageously distributes the process fluid fed via port 18 to the bottom of the catalyst bed. The process fluid then passes through the catalyst bed in opposite directions and reacts under the appropriate conditions to form methanol. The resulting process fluid is then collected around the middle of the reaction vessel by the tubular ring collector. The process fluid enters a chamber defined by the ring 24 via the orifices 34, passes into conduit 26 and thence conduits 28, 30 and 32 that then allow it to be removed from the vessel via ports 20 and 22.

The method of adapting an axial flow reactor comprising shell 10, ends 12 and 14 and opposed ports 16, 18, 20 and 22, to that depicted in FIG. 1 may be performed by installing in modular form, the conduits 30, 32, 28, 26 and tubular ring collector 24 via the access port 17. Conduits 30 and 32 require connection to ports 20 and 22 respectively. The conduit supporting means 36/40 are conveniently the existing catalyst restraint means and ports 20 and 22 are conveniently the existing catalyst discharge ports. Hence following adaptation according to the method of the present invention, ports 16 and 18 are process fluid inlet ports and ports 20 and 22 are process fluid outlet ports.

Figure 2:
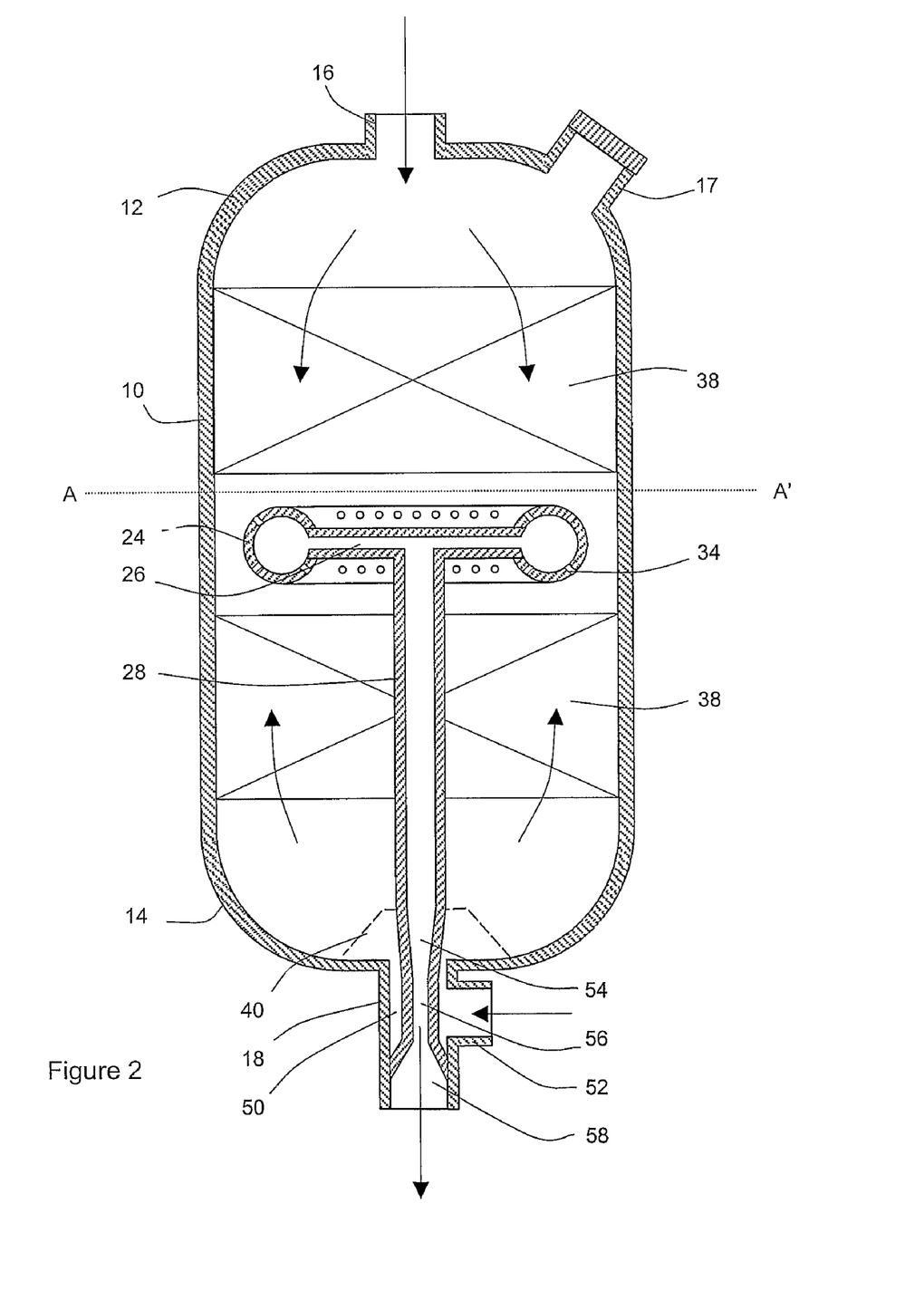
FIG. 2 is a diagrammatic vertical cross section of an opposed axial flow reaction vessel adapted according to a second embodiment of the present invention.

In FIG. 2, the reaction vessel again comprises shell 10, domed ends 12 and 14 and ports 16, 17 and 18. Ports 20 and 22 either side of port 18 are omitted. Prior to adaptation, ports 16 and 18 were process fluid inlet and outlet ports respectively.

The process fluid collection means comprising perforate tubular ring collector 24, conduit 26 and conduit 28 are similarly located but conduit 28 is not connected to ports 20 and 22. Rather conduit 28 extends down through the perforate catalyst restraining means 40 and into port 18 forming itself an outlet port and defining an annulus 50 into which process fluid may be fed via a new port 52 beneath the domed end 14 in the side of port 18. Conduit 28 widens at its end to seal port 18 below port 52 so that the process fluid fed via port 52 must move upwards through port 18 and the perforate restraining means 40 and into the catalyst bed. Conduit 28 as it extends out of port 18 is formed to provide a venturi section. The venturi section is formed by constricting the diameter of conduit 28 to form a higher pressure zone 54 above the constriction 56, a lower pressure zone at the constriction and a gradual expansion for pressure recovery leading to an exit zone 58. The constriction 56 may be located conveniently where the port 52 accesses port 18 so that the process fluid may more readily flow through annulus 50 and into the vessel.

In use for the synthesis of methanol, approximately equal amounts of dewatered synthesis gas comprising hydrogen and carbon oxides, optionally with unreacted gas recycled from methanol recovery, are fed through ports 16 and 18. Process fluid is fed to port 18 via port 52 and annulus 50. Distributor means (not shown) distribute the gas entering via port 16 over the surface of the top of the catalyst bed. The existing perforate catalyst restraining means 40 acts to distribute the process fluid fed via port 18 to the bottom of the catalyst bed. The process fluid then passes through the methanol synthesis catalyst bed in opposite directions and reacts under the appropriate conditions to form methanol. The resulting process fluid is then collected around the middle of the reaction vessel by the tubular ring collector. The process fluid enters the ring 24 via the orifices 34, passes into conduit 26 and thence conduit 28. The process fluid passes though conduit 28 to the venturi before being removed from the reaction vessel via port 18.

The method of adapting an axial flow reactor comprising shell 10, ends 12 and 14 and opposed ports 16 and 18 to that depicted in FIG. 2 may be performed by installing in modular form, the extended conduit 28, conduit 26 and tubular ring collector 24 via the access port 17. The existing perforate catalyst restraining means 40 requires adaptation to allow access for extended conduit 28 and a new port 52 is required in the side of port 18. Hence following adaptation according to the method of the present invention, ports 16 and 18 (via port 52) are process fluid inlet ports and conduit 28 forms the outlet port through port 18.

This embodiment is applicable to existing vessels that do not have catalyst discharge ports 20, 22 or other such ports suitable for adaptation. An advantage of this embodiment is that it does not require internal connection, e.g. by welding, within the reaction vessel, making connection of the process fluid collection means simpler by enabling thermal stress relieving to be more readily carried out on site.

In FIG. 3, the reaction vessel again comprises shell 10, domed ends 12 and 14 and ports 16, 17, 18, 20 and 22. However in this embodiment following adaptation the process fluid is fed into the vessel via ports 20 and 22 and inserted conduits 60 and 62 that pass through ports 20 and 22 respectively and into the catalyst bed. Distributor means (not shown) on the ends of each of conduits 60 and 62 may be provided to distribute the process fluid evenly into the catalyst bed. The process fluid collection means comprising perforate tubular ring collector 24, conduit 26 and conduit 28 are of similar form to that depicted in FIG. 2 in which conduit 28 extends down through the perforate catalyst restraining means 40 and into port 18 to which it is connected, however no venturi means or port 52 are required.

In use for the synthesis of methanol, approximately equal amounts of dewatered synthesis gas comprising hydrogen and carbon oxides, optionally with unreacted gas recycled from methanol recovery, are fed through ports 16 and 20/22, i.e. about half though port 16 and one quarter through each of ports 20 and 22. Process fluid fed to port 16 is distributed over the top of the catalyst bed by distributor means (not shown). Process fluid fed to ports 20 and 22 passes through conduits 60 and 62, and is distributed to the bottom of the catalyst bed. The process fluid then passes through the methanol synthesis catalyst bed in opposite directions and reacts under the appropriate conditions to form methanol. The resulting process fluid is then collected around the middle of the reaction vessel by the tubular ring collector. The process fluid enters the ring 24 via the orifices 34, passes into conduit 26 and thence conduit 28. The process fluid passes though conduit 28 before being removed from the reaction vessel via port 18.

The method of adapting an axial flow reactor comprising shell 10, ends 12 and 14 and opposed ports 16, 18, 20 and 22 to that depicted in FIG. 3 may be performed by installing in modular form, the extended conduit 28, conduit 26 and tubular ring collector 24 via the access port 17. The conduits 60 and 62 may be inserted through ports 20 and 22 thereby minimising internal modifications to the reactor. As in the second embodiment depicted in FIG. 2, the existing perforate catalyst restraining means 40 requires adaptation to allow access for extended conduit 28. Hence following adaptation according to the method of the present invention, ports 16, 20 and 22 are process fluid inlet ports and port 18, connected to conduit 28 is the process fluid outlet port.

In FIG. 4, the reaction vessel again comprises shell 10, domed ends 12 and 14 and ports 16, 17 and 18. Ports 20 and 22 either side of port 18 are omitted. Prior to adaptation, ports 16 and 18 were process fluid inlet and outlet ports respectively.

The process fluid collection means comprising perforate tubular ring collector 24, conduit 26 and conduit 28 are similarly located centrally within the reactor but conduit 28 is not connected to ports 20 and 22. Rather conduit 28 extends down to be in fluid communication with port 18. By-pass tubes 70 are provided within vessel 10 that extend vertically from above the surface to bed 38 at the inlet end by port 16 to below bed 38 by outlet port 18. Only two tubes are shown disposed at the periphery of the bed 38 between the ring collector 24 and the vessel walls however it will be understood that more tubes may be provided and they need not be restricted to the periphery of the catalyst bed.

In use for the synthesis of methanol, dewatered synthesis gas comprising hydrogen and carbon oxides, optionally with unreacted gas recycled from methanol recovery, is fed through port 16. The entire process fluid is fed to the reactor through port 16. A portion about 50% by volume of the synthesis gas then passes through by-pass tubes 70 to below the catalyst bed. Distributor means (not shown) may be used to distribute the gas entering via port 16 over the surface of the top of the catalyst bed and from the bottom of tubes 70 over the bottom of the bed. The portions of synthesis gas then pass through the methanol synthesis catalyst bed in opposite directions and reacts under the appropriate conditions to form methanol. The resulting process fluid is then collected around the middle of the reaction vessel by the tubular ring collector. The process fluid enters the ring 24 via the orifices 34, passes into conduit 26 and thence conduit 28. The process fluid passes though conduit 28 to outlet port 18.

The method of adapting an axial flow reactor comprising shell 10, ends 12 and 14 and opposed ports 16 and 18 to that depicted in FIG. 4 may be performed by installing in modular form, the extended conduit 28, conduit 26 and tubular ring collector 24 via the access port 17. The existing perforate catalyst restraining means 40 may be removed as the conduit 28 is in direct fluid communication with port 18. The bypass tubes are inserted though port 17 and fixed in place by means of restraining means (not shown) prior to catalyst loading. Hence following adaptation according to the method of the present invention, ports 16 and 18 are process fluid inlet ports outlet ports respectively, i.e. their duty has not changed.

This embodiment is applicable to existing vessels that do not have catalyst discharge ports 20, 22 or other such ports suitable for adaptation. Whereas such ports are not depicted in FIG. 4, they may be present but be unsuitable for adaptation. An advantage of this embodiment is that the process fluid need not be split for feeding to the vessel and the existing inlet and outlet ports remain in their original duty, thereby removing the need for extra pipework. The process fluid collection means are also simpler than those depicted in FIGS. 1-3.

The invention claimed is:

1. A method of adapting a reaction vessel comprising a shell having opposed ports from a configuration for providing axial flow to a configuration for providing opposed flow, said method comprising:
   (i) installing process fluid collection means centrally within the shell and in fluid communication with one or more outlet ports of said ports, wherein said process fluid collection means comprise a perforate member defining a chamber and a conduit in fluid communication with said chamber, said conduit being adapted for attachment to said one or more of said outlet ports,
   (ii) providing the vessel with a bed of particulate catalyst or sorbent around said process fluid collection means; and
   (iii) adapting the vessel to direct a process fluid fed to the vessel through one or more inlet ports of said ports such that the process fluid is passed axially and in an opposite direction through said fixed bed of catalyst or sorbent and is collected by said process fluid collection means.

2. The method according to claim 1 wherein the process fluid collection means comprises a perforate ring collector.

3. The method according to claim 1 wherein the process fluid collection means is in modular form and the collection means are joined together in-situ within the vessel.

4. The method according to claim 1 wherein the process fluid collection means is installed in fluid communication with two or more of said outlet ports.

5. The method according to claim 1, wherein the process fluid collection means are installed in fluid communication with one of said outlet ports, said one outlet port being in concentric arrangement with one of said inlet ports.

6. The method according to claim 5, wherein the one outlet port comprises venturi means.

7. The method according to claim 1 further comprising providing by-pass tubes within the vessel that extend vertically from above the upper surface of the bed to below the bottom surface of the bed.

* * * * *